United States Patent [19]

Jerosch-Herold et al.

[11] Patent Number: 5,289,124
[45] Date of Patent: Feb. 22, 1994

[54] PERMEABILITY DETERMINATION FROM NMR RELAXATION MEASUREMENTS FOR FLUIDS IN POROUS MEDIA

[75] Inventors: Michael Jerosch-Herold, High Bridge; Hans Thomann, Bedminster, both of N.J.

[73] Assignee: Exxon Research and Engineering Company, Florham Park, N.J.

[21] Appl. No.: 763,026

[22] Filed: Sep. 20, 1991

[51] Int. Cl.⁵ .................................... G01R 33/20
[52] U.S. Cl. .................................... 324/303; 324/300
[58] Field of Search ............... 324/300, 303, 307, 309, 324/312, 313, 314

[56] References Cited

U.S. PATENT DOCUMENTS

| | | | |
|---|---|---|---|
| 4,719,423 | 1/1988 | Vinegar et al. | 324/303 |
| 4,728,892 | 3/1988 | Vinegar et al. | 324/309 |
| 4,933,638 | 6/1990 | Kenyon et al. | 324/303 |
| 5,023,551 | 6/1991 | Kleinberg et al. | 324/303 |
| 5,055,788 | 10/1991 | Kleinberg et al. | 324/303 |

Primary Examiner—Michael J. Tokar
Assistant Examiner—Raymond Y. Mah
Attorney, Agent, or Firm—Ronald D. Hartman

[57] ABSTRACT

The present invention is a method to rapidly determine the fluid-flow permeability of porous media with nuclear magnetic resonance (NMR). The method can be applied to measurements of permeability in fluid-saturated earth formations using NMR logging tools.

8 Claims, 8 Drawing Sheets

PERMEABILITY DETERMINATION FROM NMR RELAXATION MEASUREMENTS FOR FLUIDS IN POROUS MEDIA

BACKGROUND OF THE INVENTION

The present invention relates to a method for determining the fluid flow permeability of porous media. In particular, the present invention relates to measuring the permeability by nuclear magnetic resonance (NMR) using the $T_2$ relaxation time for the decay of the transverse magnetization of fluids saturating the medium under investigation.

The properties of fluids in porous media are of great relevance in many fields of science and engineering. There are numerous measurements which bear some importance on characterizing fluid properties in confined geometries like sandstone rocks. We list here a few: porosity, fluid flow permeability (both dc and ac), electrical conductivity, wettability, etc. Quantities like porosity and fluid flow permeability in porous rocks are of great relevance for determining, the producibility of petroleum reservoirs.

For porous media it has become customary to speak of the solid material which forms the "backbone" as the matrix and its complement as the pore space. Porosity is defined as the ratio of pore space volume inside the porous material to the total volume of the porous medium. Permeability is a measure for the ability of porous materials like e.g. porous rocks to permit fluid flow through the pore space. It generally increases with porosity, but also depends on other parameters of the rocks as e.g. the specific surface area of the pore space, the pore size distribution and the pore shape. The fluid flow permeability can vary by about 8 orders of magnitude in loose sediments and sedimentary rocks. It has the dimension of area and is defined by d'Arcy's law which relates the rate of fluid flow to the pressure differential between two parallel planes for inflow and outflow. The fluid flow permeability is measured in the laboratory by fitting sleeves to core samples which are often cylindrically shaped. The top and bottom of the core samples are connected to fluid inlets and outlets and a known pressure difference is applied across the sample. The fluid flow rate is measured for a set of different pressure gradients. Liquids or gases can be used as flowing medium, although the measurement using a liquid is generally easier as in most cases the liquid can be considered incompressible. The laboratory procedure therefore requires first to drill core plugs from core samples, which have to be cleaned with various solvents. In contrast the method of the present invention can be carried out with a nuclear magnetic resonance logging tool to measure in situ the transverse relaxation time of the fluids saturating an earth formation to accurately predict the fluid flow permeability of the earth formation.

Nuclear magnetic resonance (NMR) has been employed for some time to study fluids permeating the pore space of porous media [see J. R. Banavar and L. M. Schwartz. "Molecular Dynamics in Restricted Geometries", chapter 10, edited by J. Klafter and J. M. Drake, J. Wiley (1989)]. The fluid supplies the probe particles which diffuse in the pore space. Since the classic paper by Brownstein and Tarr (BT) [see K. R. Brownstein and C. E. Tarr, *Physical Review* A. 19, 2446 (1979)] it has been realized that nuclear spin relaxation can provide information about the pore space geometry. BT discussed the case of $T_1$ and $T_2$ relaxation in an isolated pore where the nuclear spins are relaxed by collisions with the pore walls. The interpretation of $T_1$ measurements with this model for fluids in porous media can present several problems. It is assumed that the relaxation of the bulk fluid in the pore space is negligible in comparison with the surface relaxation. In the limit where the nuclear spins diffuse at a fast rate to the pore surface and the surface relaxation is in comparison relatively slow, the averaged relaxation curve can be related to the pore size probability distribution. In this so called fast diffusion limit where the lowest order relaxation mode dominates one still has to assume that the surface relaxation strength is uniform and the pores are isolated to relate the distribution of relaxation times uniquely to the pore size distribution. It is conceivable to have porous samples with the same pore size geometry but different levels of paramagnetic impurities which influence the surface relaxation velocity while the fluid flow permeability would remain unchanged. To obtain a reliable estimate of the fluid flow permeability with NMR one therefore has to perform an experiment which directly probes fluid transport in the porous medium like for example the diffusion of fluid molecules in the pore space. For $T_1$ measurements the nuclear spin relaxation depends on the rate at which magnetization is carried to the surface but also on the surface relaxation velocity $\rho$. As the surface relaxation strength $\rho$ has no bearing on permeability one can therefore hope to correlate $T_1$ and the fluid flow permeability only for classes of materials with similar surface relaxation properties.

There is an increasing interest in applying NMR in well-bore environments to determine the properties of fluid carrying earth formations [see P. N. Sen. C. Straley, W. E. Kenyon and M. S. Whittingham, *Geophysics*, 55, 61-69(1990)]. This interest has been spurred by the introduction of a new generation of NMR logging tools by NUMAR [see [M. N. Miller, A. Paltiel. M. E. Gillen, J. Granot and J. C. Brouton, Society of Petroleum Engineers, SPE 20561, 321(1990)], which are already being used in the field. The new NMR logging tools are very well fitted to carry out the physical measurements required for our method of invention.

In the present invention, a measurement of the transverse relaxation time $T_2$ for fluids in porous media is used to determine the permeability of the medium by taking advantage of magnetic field inhomogeneities across pores. For strong magnetic fields and in the fast diffusion limit the relaxation is determined to first order by the transport of magnetization through the pore space and not the surface relaxation velocity. It will be shown that it is possible to correlate $T_2$ to a length characteristic of the pore space geometry which can also be determined independently from mercury injection experiments and thereby relate $T_2$ to the fluid flow permeability. It is also feasible to study the degree to which the diffusion of fluid molecules is restricted by the pore space geometry. $T_2$ for fluids in porous media is in general orders of magnitude shorter than $T_1$ in marked contrast to the situation for bulk fluids. The main mechanism for $T_2$ relaxation of the fluid spins in strong magnetic fields is due to the internal random magnetic field gradients generated by the difference in magnetic susceptibility for the fluid filling the pore space and the material making up the matrix of the porous medium. The spatial dependence of the internal gradients is determined by the pore space geometry and pore size distribution. The internal gradients in turn determine the rate at which the spins diffusing through the pore space loose their phase memory. The loss of phase memory can be monitored with a multi spin-echo pulse sequence like the Carr-Purcell-Meiboom-Gill (CPMG) pulse sequence [see S. Meiboom and D. Gill, *Rev. Sci. Instr.*, 29, 688 (1958)].

The phenomenon of spin echoes essential to the present invention was first discovered in NMR by Erwin Hahn. In an inhomogeneous magnetic field nuclear spins will precess at a Larmor frequency, $\nu_L$, determined by the local field. After an initial radiofrequency pulse which tips the spins into a plane transverse to the direction of the applied static magnetic field the spins are all in phase and the sum of the total transverse magnetization is at the maximum possible value. Due to the spread in precession frequencies the spins will dephase and the macroscopic magnetization measured with the NMR instrument will decay. It is useful to remember here that the macroscopic magnetization is a vector sum of the magnetic moments of the spins which vanishes when the phases of the magnetic moments are random. One can reverse the dephasing process by applying a 180 degree pulse a time $\tau/2$ after the initial radio-frequency pulse which tipped the nuclear spins into the transverse plane. Immediately after this pulse a spin which precesses at a faster frequency than the average lags behind by an angle which is exactly the same angle by which it was ahead of the average immediately before the 180 degree pulse. Similarly spins precessing at a frequency slower than the average are now ahead. A time $\tau/2$ after the 180 degree pulse the spins will be again be in phase and one can observe a spin-echo. Spins diffusing will be subject to different local fields between the time the first pulse was applied and the detection of the spin echo. As their Larmor frequency is not constant the refocusing of magnetization will be incomplete and the echo will be attenuated. The degree of attenuation depends on the displacement and field inhomogeneity. This attenuation can be used to measure diffusion constants in fluids and to probe the diffusion of fluid spins in the pore space of porous media.

SUMMARY OF THE INVENTION

The present invention provides a method for determining the permeability of porous media saturated with a liquid using nuclear magnetic resonance (NMR). The steps of the method include: (a) applying a radiofrequency pulse sequence which after an initial pulse generates successive spin echoes with a train of radio frequency pulses spaced apart by a time interval of length $\tau$ wherein all pulses have a carrier frequency corresponding to the Larmor frequency of the fluid spins filling the pore space of the medium for which the fluid flow permeability is to be determined; (b) measuring the decay of the transverse magnetization at each of the successive regularly spaced midpoints between the 180 degree pulses where the midpoints coincide with the peak of the spin echoes; (c) repeating steps a and b at least one more time wherein each repeat of step (a) uses said radio frequency pulse train with a different value of the pulse spacing $\tau$; (d) determining the transverse relaxation time $T_2$, from the transverse magnetization decay for each value of $\tau$, from which the relaxation time, $T_2(\tau=0)$ is obtained by extrapolation using an exponential function; (e) measuring the porosity of said porous media; (f) determining the permeability of said media from the porosity and the relaxation time $T_2$ at $\tau=0$.

In a preferred embodiment the method is performed as a down-hole well-bore measurement to swiftly and accurately determine the fluid-producing potential of an earth formation using a magnetic resonance logging system which employs static and radio-frequency magnetic fields to perform the spin-echo CPMG pulse experiment in a wellbore environment.

DESCRIPTION OF THE PREFERRED EMBODIMENT

The present invention is a method to determine the permeability of porous media using pulsed nuclear magnetic resonance. This method uses the relaxation decay of the transverse component of the magnetization ($T_2$ relaxation) measured with the Carr-Purcell-Meiboom-Gill (CPMG) pulse sequence.

Figure 6:
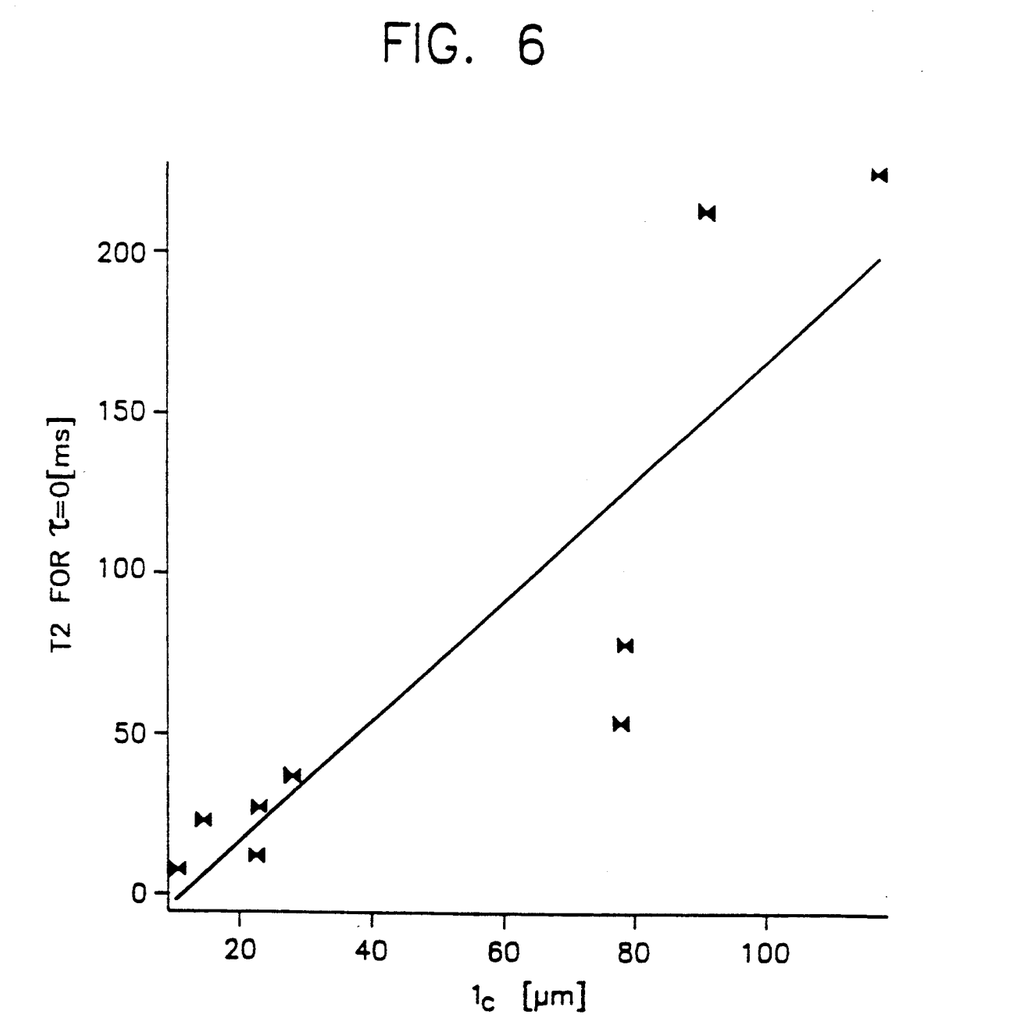
FIG. 6 shows a graph of extrapolated value of $T_2$ versus $t_c$ determined from mercury injection for sandstone rock samples.

It can be shown (see below) that the magnetization as a function of time, t is described by a stretched exponential decay function of the form:

$$m(t) \propto \exp[-(t/T_2)^\beta], \tag{1}$$

where $\beta$ is the stretch exponent. A nonlinear least squares fit of the measured values of magnetization m(t) to the stretched exponential function determines the the relaxation time $T_2$ and the stretch exponent, $\beta$. If the pulse spacing, $\tau$, is changed in incremental steps, a set of stretched exponential curves is produced yielding different values for $T_2(\tau)$. The set of $T_2$ values for different $\tau$'s follow a single exponential decay. The value of $T_2$ extrapolated to $\tau=0$ combined with the porosity, $\phi$, of the material gives the permeability, $\kappa$, of the porous medium according to (see FIG. 6).

$$\kappa \propto [T_2(\tau=0)]^2 \phi^2. \tag{2}$$

The proportionality constant in the above relation can be determined from a calibration experiment with a porous material of known porosity and permeability. The porosity is determined by first running an NMR experiment with a water jacket which surrounds the radiofrequency probe (e.g. of the NMR logging tool) and therefore calibrates the NMR signal for 100% porosity. To prevent the interference from local radio signals one can enclose the probe and water jacket in a Faraday cage. As the NMR signal is directly proportional to the number of hydrogen nuclei in the sensitive volume of the probe it will scale linearly to lower porosities. Only the contribution from liquid phases or non-adsorbed fluid will be recorded if the dead time of the instrument is set accordingly. The temperature of the fluid in the sensitive volume is of secondary influence. In a bore hole environment this varies with depth and can be compensated for by measuring the bottom temperature and temperature gradient. The NMR signal amplitude changes as a function of temperature as $1/T$.

THEORETICAL BACKGROUND

The magnetization of the fluid spins diffusing in the pore space satisfies the following modified Bloch equation:

$$\frac{\partial M}{\partial t} = D\nabla^2 M - \frac{M}{T_b}. \tag{3}$$

$T_b$ is the bulk relaxation rate of the fluid in the pore space and D is the diffusion constant which is on the order of $2 \times 10^9 [m^2/sec]$ for water at room temperature. The boundary condition is:

$$Dn \cdot \nabla M + \rho M|_{surface} = 0, \tag{4}$$

where $\rho$ is the surface relaxation velocity, which has units of length over time and can be thought of as the relaxation rate at the surface multiplied by the thickness of the layer of fluid spins relaxing near the surface. The bulk relaxation rate can always be factored out of the solution.

$$M(r,t) = m(r,t)\exp(-t/T_b) \tag{5}$$

The Bloch equation becomes:

$$\frac{\partial m}{\partial t} = D\nabla^2 m \tag{6}$$

Brownstein and Tarr expressed the general solution as a sum of normal modes:

$$m(t) = m(0) \sum_{n=0}^{\infty} I_n \exp - t/T_n \tag{7}$$
$$T_0 >> T_1 >> T_2 \ldots$$

Two limiting cases can be considered for the magnetization decay which are characterized by decay constants $\tau_c$:

$$\tau_c = \begin{cases} r^2/D \text{ diffusion limited; } \rho r/D >> 1 \\ r/\rho \text{ fast diffusion: } \rho r/D << 1 \end{cases} \tag{8}$$

In the fast diffusion case the magnetization is approximately uniform across an isolated pore and only the lowest mode in the above eigenmode expansion contributes significantly to the magnetization decay. In this limit, $\rho r/D < 1$, and when the pores are approximately isolated (narrow throat limit) one obtains for m(t):

$$m(t) = \exp\left(-\frac{\rho S}{V}t\right) \tag{9}$$

S and V are the surface area and the volume of a pore. For a pore size distribution the relaxation is described by:

$$m(t) = \int_0^\infty P(r)r^3 \exp\left(-\frac{\rho}{r}t\right)dr. \tag{10}$$

Thompson et al [see A. H. Thompson, S. W. Sinton, S. L. Huff, A. J. Katz. R. A. Raschke and G. A. Gist, *Journal of Applied Physics*, 65, 3259 (1989)] found that the pore size distribution of many porous rocks is well represented by the following class of functions:

$$P(r)dr \propto \exp[-(r/\Delta)^{\beta/(1-\beta)}]dl \tag{11}$$

and where $\Delta$ is a measure of the width of the pore size distribution and $\beta$ lies between 0 and 1. A $\beta$ value of $\frac{2}{3}$ will yield a Gaussian pore size distribution. This type of pore size distribution will lead to a stretched exponential decay in the fast diffusion limit:

$$m(t) \propto \exp[-(t/T_{1,2})^\beta]. \tag{12}$$

This result is obtained by using the saddle point method on the integral in equation (10), i.e., we determine the pore size radius for which the exponent of the integrand goes through a maximum as a function of pore radius r.

Equation 12 is of a form observed experimentally for $T_1$ and $T_2$ magnetization decays for fluids in porous media for a broad set of experimental conditions, although it was derived for the case of surface induced relaxation. We wish to arrive at an expression which explicitly accounts for the contribution to the $T_2$ decay from diffusion of fluid spins in porous media in the presence of random internal gradients. The random magnetic field gradients lead to dephasing of the nuclear spins which can only be partially compensated with a spin-echo sequence as they diffuse. As a starting point we use an expression derived by Robertson and Neuman and experimentally confirmed by Wayne and Cotts for the decay of the transverse magnetization in the presence of a uniform gradient G [see B. Robertson *Physical Review*, 151(1), 273 (1966), R. C. Wayne and R. M. Cotts, *Physical Review*, 151(1), 263 (1966) and C. H. Neuman, *The Journal of Chemical Physics*, 60 (11), 4508 (1974)]. Neuman produced expressions for the case where the spins are assumed to diffuse in a bounded medium of spherical geometry and the Carr-Purcell spin-echo sequence with spacing of the $\pi$ pulses given by $\tau$ is being used:

$$m(t) = m_0 \exp\left(-\frac{2\gamma^2 G^2 a^4 t}{D} \times \sum_{i=1}^{\infty} \frac{1}{\alpha_i^4(\alpha_i^2 - 2)}\left(1 - \frac{3 - 4e^{-\alpha_i^2\theta/2} + e^{-\alpha_i^2\theta}}{\alpha_i^2\theta}\right)\right) \tag{13}$$

$\theta = 2\tau D/r^2$ and the $\alpha$ are determined from tan $\alpha_i = -2\alpha_i/(2-\alpha_i^2)$ whose solutions asymptotically approach: $\alpha_i = i \cdot \pi$. For small $\pi$ the above expression agrees with the well-known expression for transverse relaxation of spins due to unrestricted diffusion in a uniform gradient:

$$m(t) = m_o \exp[-\gamma^2 G^2 \tau^2 Dt/3]. \quad (14)$$

Since porous media are characterized by a distribution of pore sizes the internal gradients should be parametrized in terms of pore size length. To this end we make the reasonable assumption that the magnetic field gradient across a pore of radius $r$ is inversely proportional to the pore radius:

$$G = \mu_0 H_0 \Delta \chi / r. \quad (15)$$

$\Delta \chi$ is the susceptibility difference and $\mu_o$ the magnetic permeability of vacuum. This means that under this model the gradient is uniform over individual pores but varies from pore to pore. The contribution of the spins in each pore has to be weighted by the volume of the pore. For a pore size distribution we must average the magnetization decay, m(t), over the pore size distribution in a fashion similar to the example in equation 10. We therefore arrive at the following expression for the contribution to the transverse magnetization of the spins diffusing in random internal gradient fields:

$$m(t) \propto \int_0^\infty dr\, P(r) r^3 \times \exp\left(-\frac{2\gamma(\mu_0 H_0 \Delta \chi^2 a^2 t}{D} \sum_{i=1}^\infty \frac{1}{\alpha_i^4(\alpha_i^2 - 2)} \left(1 - \frac{3 - 4e^{-\alpha_i\theta/2} + e^{-\alpha_i\theta}}{\alpha_i\theta/2}\right)\right) \times \exp -\rho\left(\frac{S}{V}\right) t. \quad (16)$$

This expression is the basis for numerical calculations performed for a series of pore size distributions (see R. L. Kleinberg and M. A. Horsfield, *Journal of Magnetic Resonance*, 88, 9–19 (1990). We numerically calculated the CPMG echo decay curve with the sum over the roots $\alpha_i$ being approximated up to the 20th term. The pore size distribution is of the form shown in Equation 11. The simulations were carried out in the same manner as the experiment. The CPMG decays were calculated for a set of values of $\tau$. We observe that the calculated magnetization decays are well described by stretched exponential functions. This suggests that equation 12 applies to a broader class of relaxation decays than suggested by the derivation which only considered surface induced relaxation. Indeed the numerical results show that the decay of the magnetization due to diffusion in the presence of random magnetic field gradients and averaged over a pore size distribution also leads to stretched exponential decays.

Figure 1A:
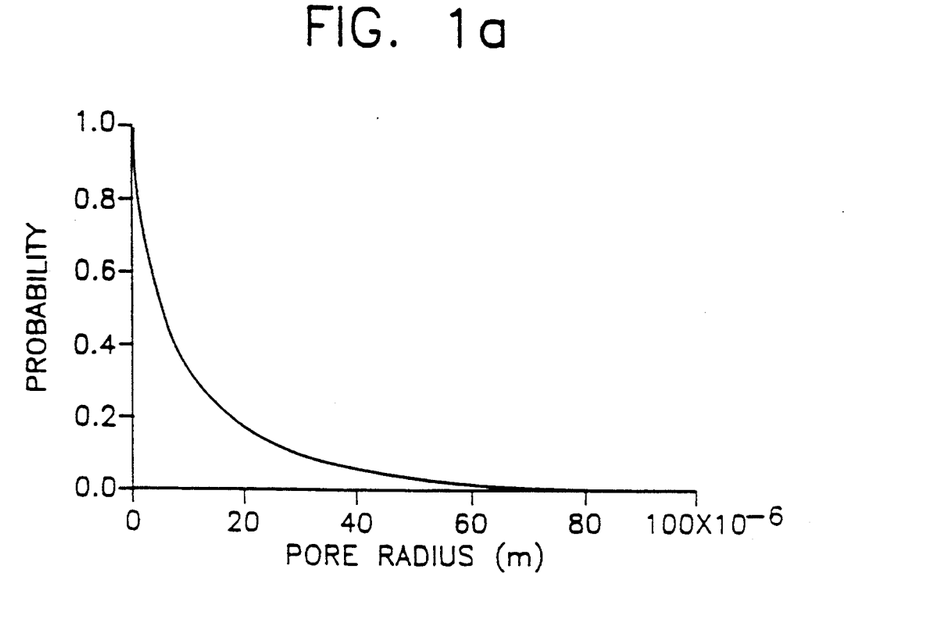
FIG. 1a shows pore size distribution calculated with equation 11.
Figure 1B:
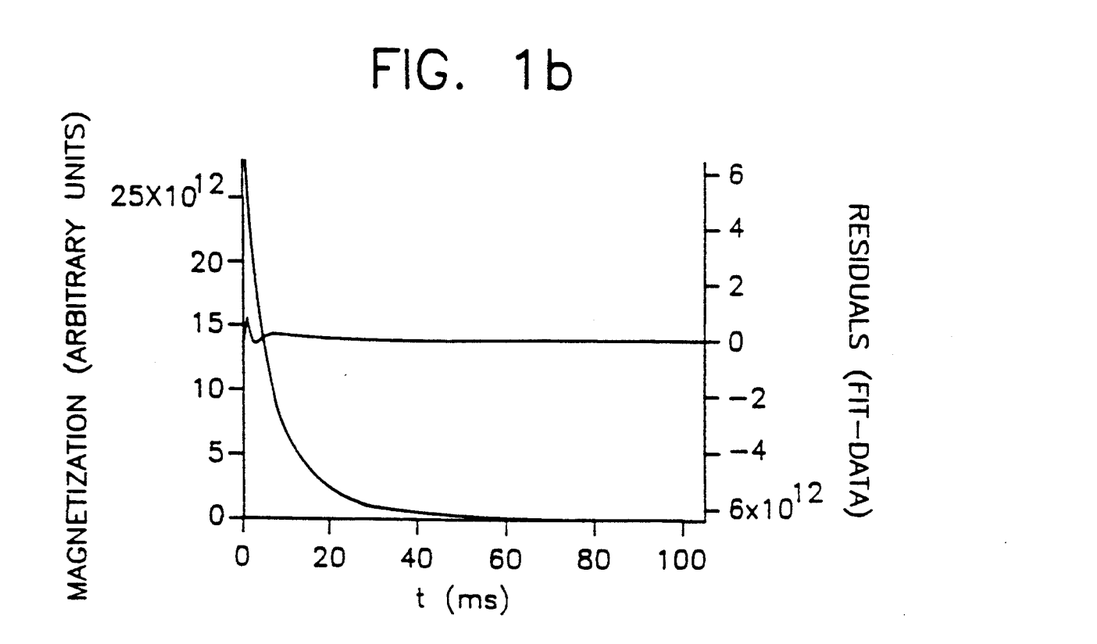
FIG. 1b shows the numerically evaluated CPMG decay for a certain $\tau$ value and the pore size distribution shown in (1a)
Figure 1C:
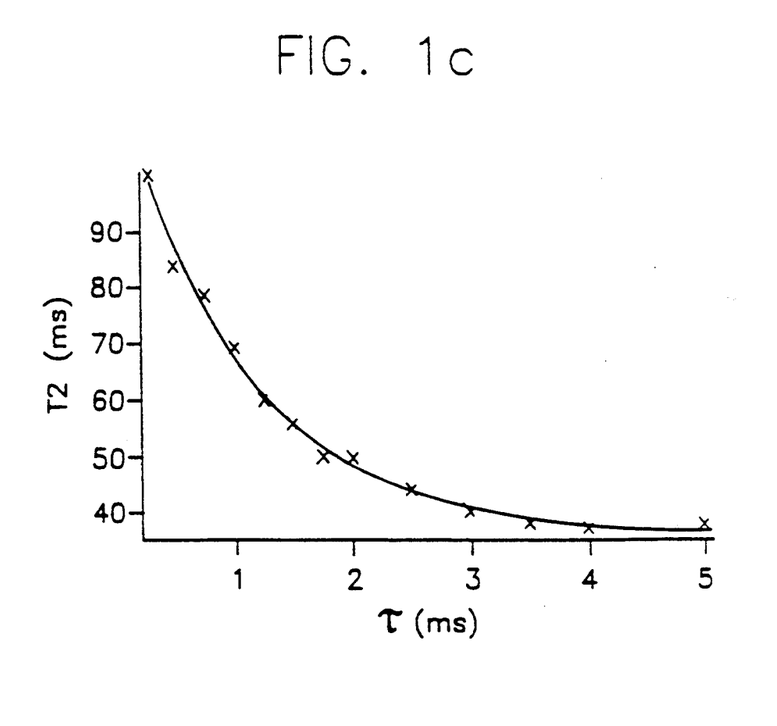
FIG. 1c shows the $T_2$ values calculated from computer simulated CPMG decays for the same pore size distribution.
Figure 2:
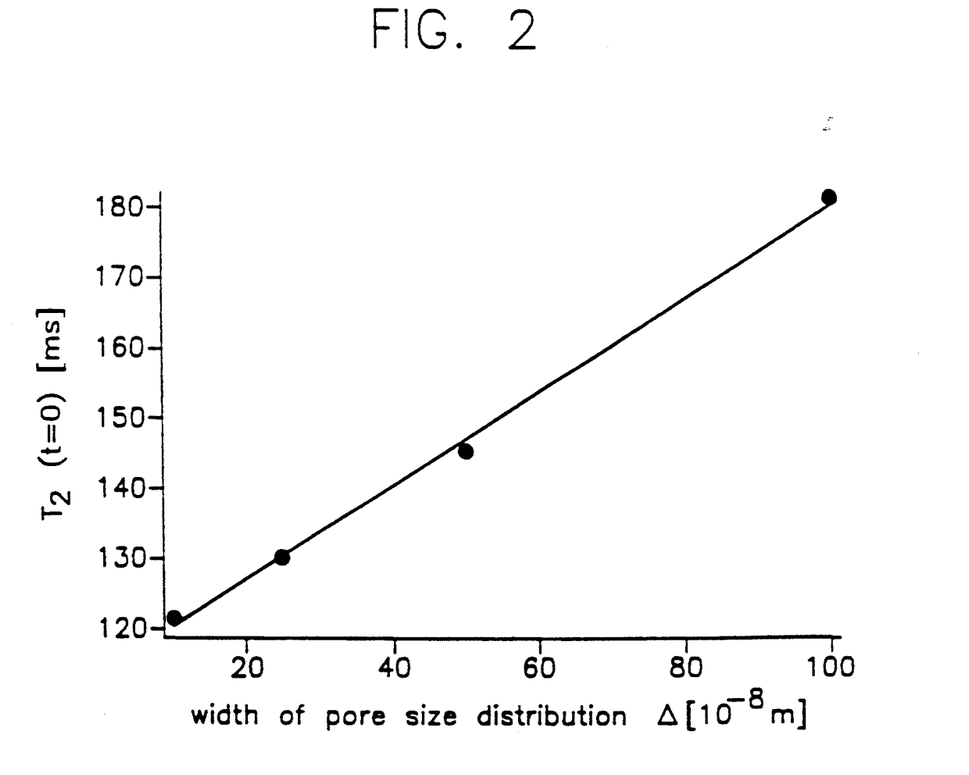
FIG. 2 shows the values of $T_2(\tau=0)$ obtained from numerical calculations for a set of pore size distributions versus the width $\Delta$ of the pore size distribution.

FIG. 1a shows the pore size distribution calculated from eq. 11 for typical values of $\Delta$ and $\beta$. FIG. 1b shows the magnetization decay calculated for the pore size distribution of 1a from equation 16. This calculation was repeated for several values of $\tau$ and the nonlinear least squares fits to the stretched exponential function yield values for $T_2$ and $\beta$. FIG. 1c shows the $T_2$ values thus obtained for a set of $\tau$ values. The set of $T_2$ values as a function of $\tau$ were than fit to an exponential function and the quality of the fit was for all cases good as can be seen from the example of FIG. 1c. We repeated this procedure for a set of pore size distributions where we arbitrarily changed $\Delta$ and $\beta$ to change the shape of the pore size distribution. It can be shown using percolation theory [see A. H. Thompson, S. W. Sinton, S. L. Huff, A. J. Katz, R. A. Raschke and G. A. Gist, *J. Appl. Phys.*, 65(8), 3259 (1989)] that $\Delta \propto \iota_c$ and $\iota_c$ is the characteristic pore size obtained from mercury injection. If we plot the extrapolated value of $T_2$, $T_2(\tau=0)$, versus the pore size distribution width $\Delta$, we observe a linear correlation.

The proportionality of $T_2(\tau=0)$ to $\Delta$ (or $\iota_c$) allows one to use $T_2(\tau=0)$ to predict the fluid flow permeability. Katz and Thompson have shown that the absolute permeability $\kappa$ of a porous medium with a broad distribution of pore sizes is related to a characteristic length $\iota_c$ by:

$$k = \frac{1}{126} l_c^2 \phi^2. \quad (17)$$

$\iota_c$ in a percolation model represents the largest pore size such that all pores with a diameter $d \geq \iota_c$ form an infinite connected cluster across the pore space. As $T_2(\tau=0) \propto \Delta \propto \iota_c$ this means that $$\kappa \propto [T_2(\tau=0)]^2 \phi^2. \quad (18)$$

This relationship is important in predicting the fluid flow permeability from NMR measurements.

The theory given to explain the present invention is presented for the sake of illustration only and is not intended to necessarily limit the scope of the claimed invention.

EXPERIMENTAL PROCEDURE

The method of this invention was tested in the laboratory using a nuclear magnetic resonance spectrometer whose functionality can replicate the capabilities of an NMR logging tool instrument. The samples used were sandstone core plugs from various geological formations in North America. For all porous samples we used the following procedure to prepare the samples: The samples were placed in a sealed container and imbibed with water. After imbibing a core plug with water for several hours it was taken out, sealed with Teflon tape and transferred to an NMR glass tube for measurements. In between measurements the samples were kept under water in a sealed container.

TABLE 1

Sandstone samples and their prorosity, permeability and $l_c$ determined independently of the NMR measurements.

| sandstone type | $l_c$ [μm] | porosity [%] | permeability [md] |
|---|---|---|---|
| Berea | 14.6 | 20.5 | 273 |
| Marsing No. 2 | 118.0 | 29.5 | 54,000 |
| Red Navajo | 23.5 | 23.6 | 1138 |
| Nugget | 10.77 | 10.9 | 4.16 |
| Silver No. 1 | 23.0 | 12.2 | 1.41 |
| Layered Navajo | 28.5 | 25.1 | 883 |
| Marsing No. 1 | 78.6 | 23.9 | 1276 |
| Silver No. 2 | 79.2 | 30.2 | 21,000 |
| Table No. 2 | 91.6 | 24.1 | 3000 |

Several samples of sandstone rock were used in developing the present invention. The permeability and porosity of these samples was determined by standard methods. In addition on samples obtained from the same batch of rock cores mercury injection experiments were performed to determine a characteristic pore (throat) size $\iota_c$. Mercury is a nonwetting fluid and under an applied pressure the mercury will first penetrate the largest pores of the medium. For a certain threshold pressure the first continuous path of mercury will be formed between the two ends of the sample and this will be detectable as a jump in the electrical conductivity across the sample. The length $\iota_c$ can be calculated with the Washburn equation from the threshold pressure at which this first conducting mercury path is established across the sample. The values for permeability, porosity and $\iota_c$ for the set of sandstone samples used for the NMR experiments are listed in Table 1. These values of permeability and $\iota_c$ obtained independently from the NMR measurements will have to be compared with the predictions using $T_2(\tau=0)$.

Figure 3:
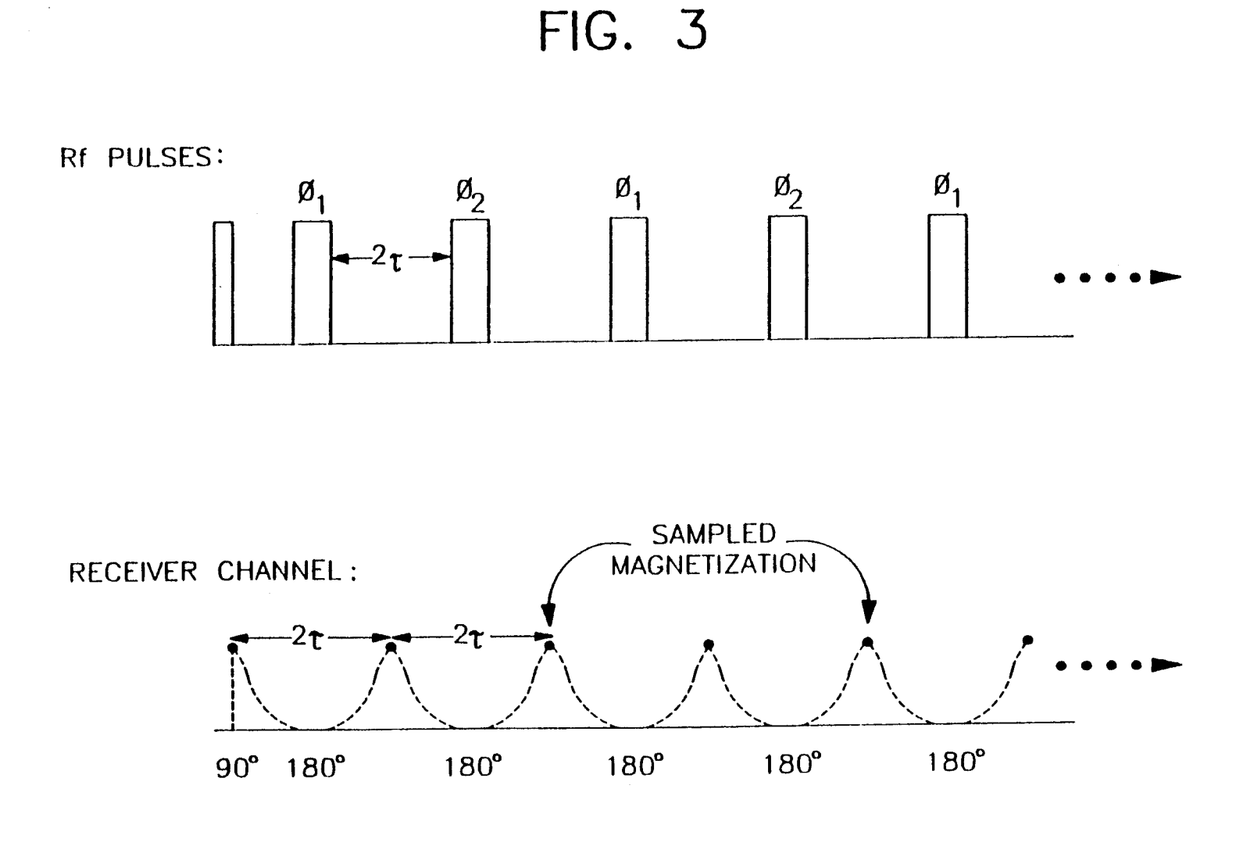
FIG. 3: Schematic diagram of the NMR spin-echo pulse sequence used for the measurement of $T_2$.

All laboratory NMR experiments were performed at a field strength of 7.05 Tesla corresponding to a Larmor frequency of the hydrogen nucleus of $\nu_L = 300.13$ MHz. The $T_1$ measurements were made with a standard inversion recovery pulse sequence. The $T_1$ measurements were only made for completeness and are not important for the development of this invention. To acquire $T_2$ data we use the Carr-Purcell-Meiboom-Gill (CPMG) pulse sequence which is comprised of an initial 90 radio frequency pulse which tips the longitudinal magnetization into the transverse plane. It is followed a time $\tau/2$ later by a train of 180 pulses with constant pulse spacing $\tau$. At the midpoint between the 180 pulses the nuclear spin magnetization of stationary spins is refocused and a Hahn echo is formed. The echo will be attenuated for spins moving along the orientation of the magnetic field gradients. The magnetization is sampled at the center of the Hahn echoes. This means that for a train of n 180° pulses we acquire n data points. We repeat this experiment for a set of $\tau$ values. This procedure corresponds exactly to one outlined above in the section titled "Method of Invention". FIG. 3 shows a schematic diagram of the pulse sequence.

When measuring the $T_2$ decay with the CPMG sequence as a function of pulse spacing, $T_2$ decreases rapidly for porous samples imbibed with water or oil. By using the CPMG pulse sequence we can ascribe this decay of $T_2$ to the effects of internal magnetic field gradients in the porous sample, which are mainly due to the magnetic susceptibility difference for the fluid imbibing the sample and the matrix. For most samples we recorded the decay of the transverse magnetization with the CPMG sequence for a set of 8-16 values of $\tau$.

DATA ANALYSIS

Figure 4A:
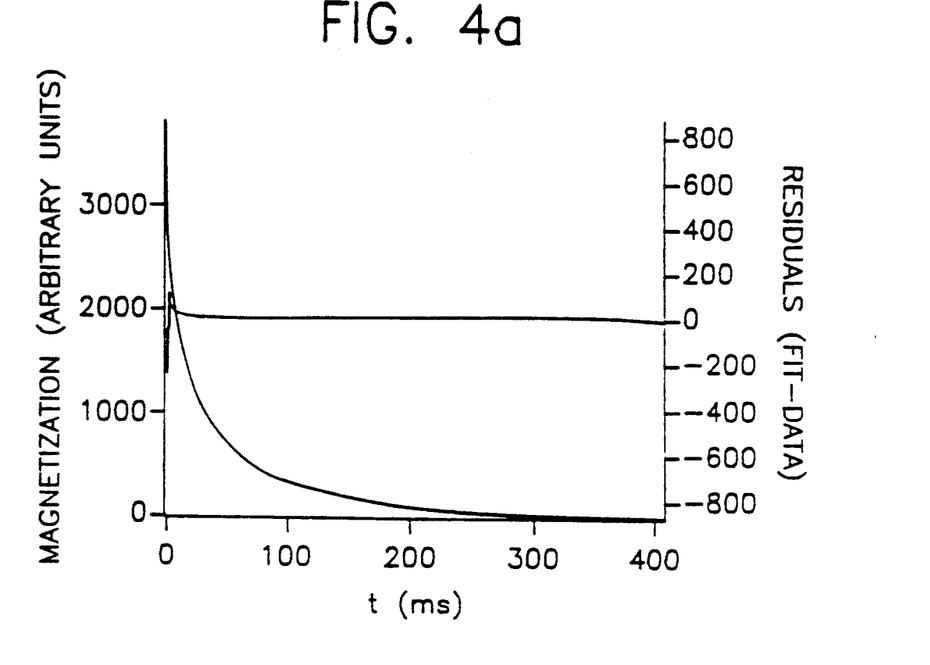
FIGS. 4a-b show an example of stretched exponential fit to CPMG decay for a water imbibed sandstone sample.
Figure 4B:
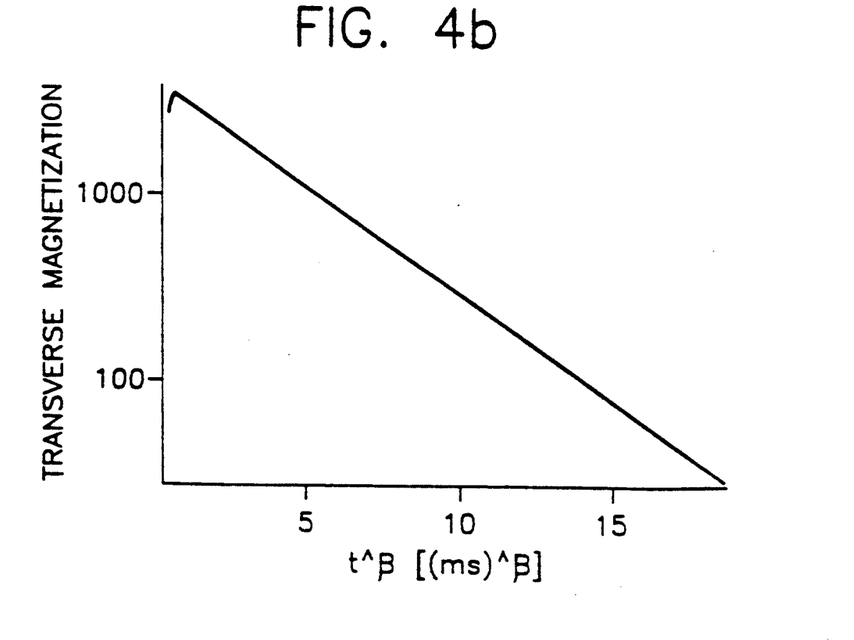

The $T_2$ magnetization decays were fit to a stretched exponential function with a nonlinear least squares fitting procedure. FIG. 4a shows an example of the stretched exponential fit to a $T_2$ CPMG decay curve. The stretched exponential function approximates the experimental data well over 2-3 orders of magnitude as can be seen from FIG. 4b. No data points were discarded before fitting the data to the stretched exponential function.

Figure 5:
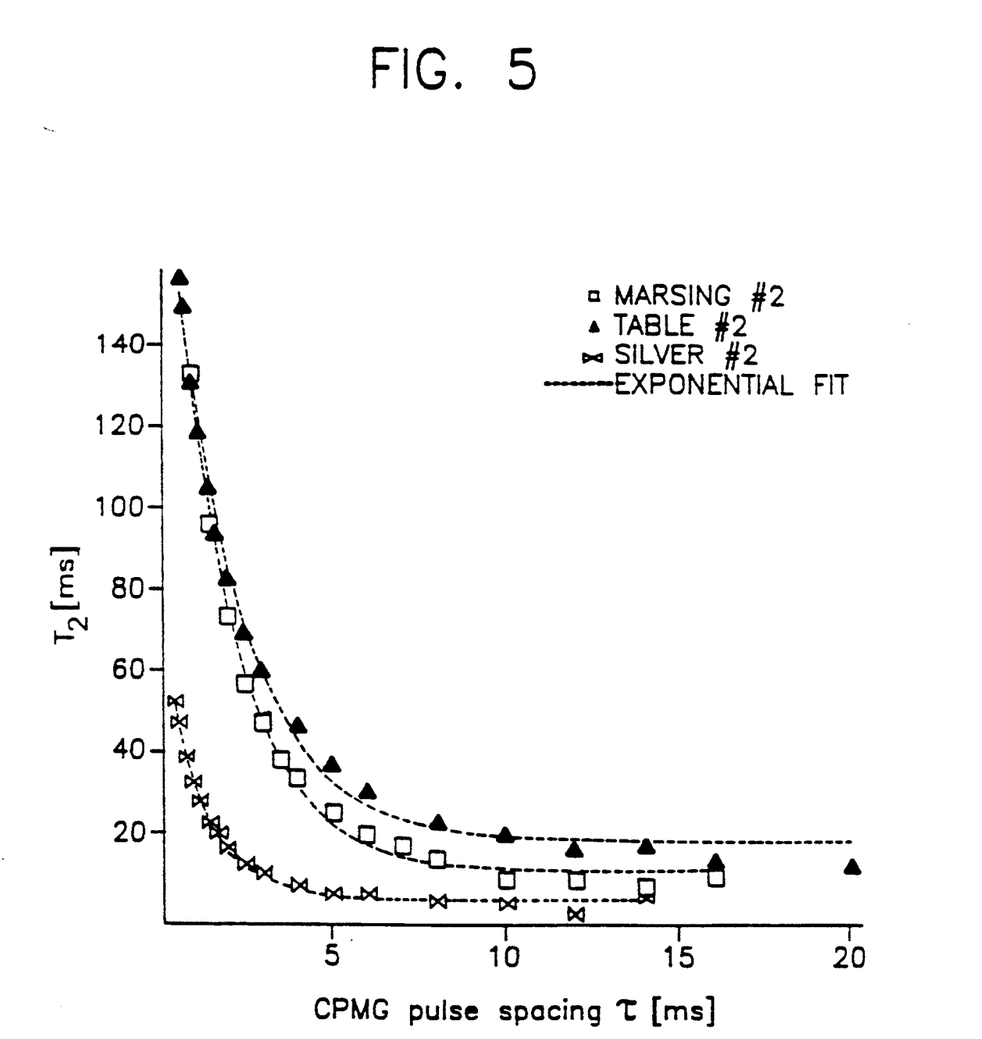
FIG. 5 shows the dependence of $T_2$ on CPMG pulse spacing $\tau$ for a set of sandstone samples. The $T_2$ values can be extrapolated to $\tau=0$ with an exponential function.

We acquired for each sample a set of CPMG decay curves by varying $\tau$. The stretched exponential fit yields a value of $T_2$ for each value of $\tau$. The composite set of data points for $T_2(\tau)$ is shown in FIG. 5 for three representative sandstone samples. We fit the resulting set of $T_2(\tau)$ data to a single exponential function. FIG. 5 shows the nonlinear least squares fits as dotted curves. This allows one to extrapolate $T_2(\tau)$ to $\tau=0$. $T_2(\tau=0)$ should therefore give a value of the transverse magnetization relaxation time $T_2$ independent of the strength of the internal magnetic field gradients and be proportional to some characteristic length of the pores. FIG. 6 shows a plot of $T_2(\tau=0)$ versus the characteristic pore diameter $\iota_c$ determined from the threshold pressure for mercury injection via the Washburn equation. Such a relationship is of great value for a rapid order of magnitude determination of permeability based on the above mentioned relationship proposed by Katz and Thompson:

$$k = \frac{1}{126} l_c^2 \phi^2.$$

Figure 7:
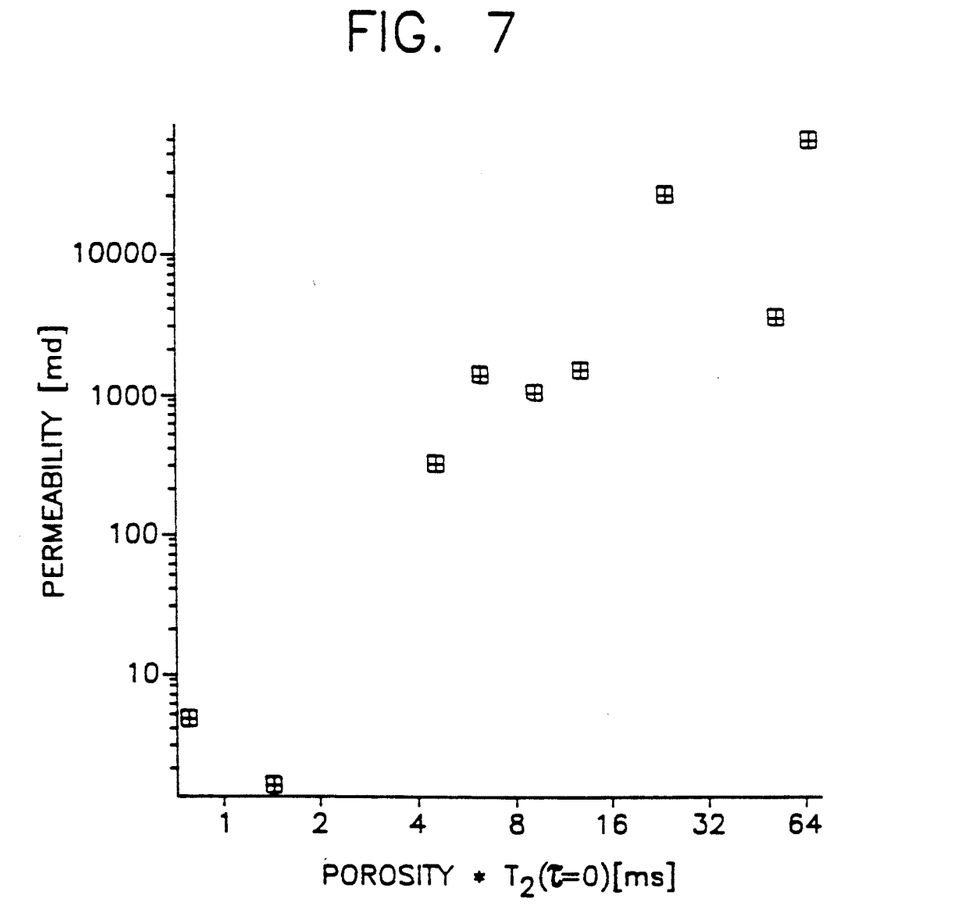
FIG. 7 shows a graph of $T_2(\tau=0) \times \Phi$ versus permeability $\kappa$ for sandstone rock samples.

And indeed as FIG. 7 shows there exists a correlation between the product of porosity $\Phi$ and $T_2(\tau=0)$ and the independently determined permeability of the porous rock samples as predicted by the relation $k \propto [T_2(\tau=0)]^2\Phi^2$. In this equation the exponent of $T_2(\tau=0)$ is predicted to be 2. However the range of the data in FIG. 7 would indicate that the exponent falls into a range of about 1.8 to 2.2. $T_2$ values obtained with the CPMG pulse sequence (which should be the method of choice) are strongly dependent on the pulse spacing $\tau$. Only when the gradient and diffusion induced relaxation is taken into account, do the resulting $T_2(\tau)$ values extrapolated to $\tau=0$ show the discussed correlations with permeability and $\iota_c$.

The present invention takes advantage of the correlations between $T_2$ determined with NMR and a characteristic pore or throat size which determines the fluid flow permeability. This characteristic length $\iota_c$ can also be determined by mercury injection but mercury injection experiments cannot be carried out in a down-hole environment. For in situ NMR relaxation time measurements in rock formations with an NMR logging tool it is feasible to carry out a $T_2$ measurement described here with the present generation of logging tools and predict the fluid flow permeability using NMR in a manner which is much less time-consuming than other methods known to date.

What is claimed is:

1. A method for determining the fluid flow permeability of porous media saturated with a liquid using nuclear magnetic resonance (NMR) and comprising:
    (a) applying a radiofrequency pulse sequence which after an initial pulse generates successive spin echoes with a train of radio frequency pulses spaced apart by a time interval of length $\tau$ wherein all pulses have a carrier frequency corresponding to the Larmor frequency of the fluid spins filling the pore space of the medium for which the fluid flow permeability is to be determined;
    (b) measuring the decay of the transverse magnetization at each of the successive regularly spaced midpoints between the 180 degree pulses where the midpoints coincide with the peak of the spin echoes;
    (c) repeating steps a and b at least one more time wherein each repeat of step (a) uses said radio frequency pulse train with a different value of the pulse spacing $\tau$;
    (d) determining the transverse relaxation time $T_2$, from the transverse magnetization decay for each value of $\tau$, from which the relaxation time, $T_2(\tau=0)$ is obtained by extrapolation using an exponential function;

(e) measuring the porosity of said porous media;

(f) determining the permeability of said media from the porosity and the relaxation time $T_2$ at $\tau=0$.

2. The method of claim 1 wherein said porous media is an earth formation and the measurement is performed in a well-bore environment with an NMR logging tool.

3. The method of claim 1 wherein said pulsed radio frequency signal is applied according to the Carr-Purcell-Meiboom-Gill (CPMG) sequence.

4. The method of claim 1 wherein the relaxation time, $T_2$ is obtained from the transverse magnetization decay in step (d) by relating the transverse magnetization to time by a stretched exponential function.

5. The method of claim 1 wherein the relaxation time $T_2$ at $\tau=0$ in step (d) is obtained by relating $T_2$ exponentially to $\tau$.

6. The method of claim 1 wherein said permeability of step (f) is obtained from the product of the porosity and the transverse magnetization, $T_2$ at $\tau=0$, wherein said porosity and T are each raised to a power.

7. The method of claim 6 wherein said power is between about 1.8 and 2.2.

8. The method of claim 7 wherein said power is 2.

* * * * *